United States Patent [19]

Manghisi et al.

[11] Patent Number: 5,382,663
[45] Date of Patent: Jan. 17, 1995

[54] PROCESS FOR THE PREPARATION OF DILTIAZEM

[75] Inventors: Elso Manghisi; Bruno Perego, both of Lomagna, Italy

[73] Assignee: Lusochimica S.p.A., Lomagna, Italy

[21] Appl. No.: 74,841

[22] PCT Filed: Dec. 9, 1991

[86] PCT No.: PCT/EP91/02353
§ 371 Date: Jun. 23, 1993
§ 102(e) Date: Jun. 23, 1993

[87] PCT Pub. No.: WO92/10485
PCT Pub. Date: Jun. 25, 1992

[30] Foreign Application Priority Data

Dec. 11, 1990 [IT] Italy .................. 22340 A/90

[51] Int. Cl.$^6$ ............................ C07D 281/10
[52] U.S. Cl. ............................ 540/491
[58] Field of Search ............................ 540/491

[56] References Cited

U.S. PATENT DOCUMENTS 4,902,684  2/1990  Floyd ................. 540/491
4,937,334  6/1990  Cavicchioli ......... 540/491

FOREIGN PATENT DOCUMENTS 158303  10/1985  European Pat. Off. .

OTHER PUBLICATIONS

Koziara, *Synthesis* 527 (1979).
Hampl, Chem Abs. 114, 207024d (1991).

*Primary Examiner*—Mark L. Berch
*Attorney, Agent, or Firm*—Bucknam & Archer

[57] ABSTRACT

(+)-Cis-3-(acetoxy)-5-[2-(dimethylamino)-ethyl]-2,3-dihydro-2-(4-methoxyphenyl)-1,5-benzothiazepin-4(5H)-one hydrochloride is prepared by N-alkylation of (+)-cis-3-hydroxy-2,3-dihydro-2-(4-methoxyphenyl)-1,5-benzothiazepin-4(5H)-one with dimethylaminoethyl chloride and $K_2CO_3$ in toluene/water, addition of a solubilizing agent and in the presence of a phase-transfer catalyst, the toluene phase being directly subjected to the final O— acetylation.

2 Claims, No Drawings

PROCESS FOR THE PREPARATION OF DILTIAZEM

The present invention relates to an improved process for the preparation of (+)-cis-3-(acetoxy)-5-[2-(dimethylamino)-ethyl]-2,3-dihydro-2-(4-methoxyphenyl)-1,5-benzothiazepin-4(5H)-one hydrochloride of formula (I):

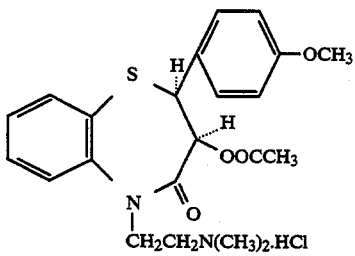

This compound, also known under the International Common Denomination of "Diltiazem", is of paramount practical importance for its important pharmacological activities.

The literature discloses several processes for preparation of compound (I). Particularly U.S. Pat. No. 3,562,257 discloses a synthesis of (I) which includes the following steps:

(+)-cis-3-hydroxy-2,3-dihydro-2-(4-methoxyphenyl)-1,5-benzothiazepin-4(5H)-one (II):

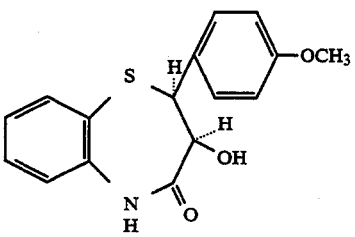

obtained as disclosed in the same U.S. Pat. No. 3,562,257, is reacted with dimenhylaminoethyl chloride of formula (III):

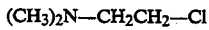

(CH₃)₂N—CH₂CH₂—Cl       (III)

to give the intermediate of formula (IV):

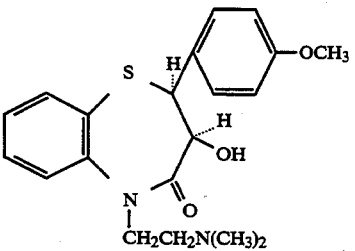

which is subsequently transformed by acetylation into the final product (I). The above mentioned U.S. Pat. No. 3,562,257 claims the following conditions for the main step, i.e. for the reaction between (II) and (III): reaction of (II) with sodium hydride, metallic sodium or sodium amide in a solvent such as dimethyl sulfoxide, dioxane, toluene or xylene, and subsequent reaction of the obtained salt with (III). Sodium hydride and dimethyl sulfoxide are respectively the preferred base and solvent. The process is unsatisfying from the safety point of view (as it is well known, the mixture NaH/(CH₃)₂SO may give rise to explosions) and under ecological aspects; it requires long times and produces large amounts of waste sewage which must be incinerated to avoid pollutions. These drawbacks have only partially been overcome by subsequently disclosed processes. For example, U.S. Pat. No. 4,438,035 (corresponding to EP 0,081,234) discloses a process to obtain compound (I), which is carried out according to the scheme reported in U.S. Pat. No. 3,562,257, but the reaction between (II) and (III) is effected using potassium carbonate in a solvent selected from acetone, a lower alkyl acetate or an acetone/water mixture. Acetone and acetone/water are preferred solvents; as tests from the applicant have demonstrated, acetone alone fits badly to this reaction, because long reaction times, up to two days, are needed to obtain good yields. Good yields are obtained with acetone/water in shorter times. A drawback of this process resides in its high ecological cost. In fact at the end of the reaction solvent must be removed and incinerated, with high costs, since it is contaminated by compound (III) and by-products and cannot by recycled.

Another drawback resides in operating in solid-liquid eterogeneous phase, with problems connected with the stirring of the reaction mixture and especially with the necessity to eliminate the salts (KCl and unreacted K₂CO₃) at the end of the reaction.

This must be accomplished with a centrifugation which requires long times, due to the physical form of the solid. The final step (the transformation of (IV) into (I)) entails acetone evaporation, redissolution in toluene and acetylation with acetic anhydride.

Finally, EP-A-158,303 discloses a process according to which the reaction between the intermediate (II) and the reagent (III) is carried out under phase-transfer conditions. Typically, an halogenated organic solvent, such as methylene chloride, chloroform or 1,2-dichloroethane, is used, optionally at the presence of a catalyst, such as a quaternary ammonium halide. Calcium or barium hydroxide in aqueous phase are normally used as halohydric acid acceptors. At the end of the reaction the solvent is evaporated and the residue is taken up in toluene for the acetylation reaction.

The drawback of this process resides especially in using a highly polluting solvent which is also of difficult elimination. It is well-known, in fact, that halocarbons always show severe problems when they must be eliminated by incineration. In this case, as the tests of Applicants demonstrate, the solvent coming from the reaction is so polluted that its recovery is not economical, therefore it is destroyed.

A further drawback consists of the necessity to change the solvent before the acetylation reaction; and it is well-known how changing solvent on an industrial level implies remarkable costs and complications.

It has surprisingly been found now that all the drawbacks of the above-mentioned processes can be overcome if the reaction between (II) and (III) is carried out in a biphasic system formed by toluene and water, in the presence of little amounts of dimethylformamide, or N,N-dimethylacetamide or N-methyl-2-pyrrolidone as solubilizing agent, of potassium carbonate as a base and of a small amount of quaternary ammonium salts as phase-transfer catalysts.

The high yields which characterize the process according to the invention are the more surprising as the use of toluene as solvent appeared not to be recommended as far as known in the prior art.

In fact, in the above-mentioned EP-A-0,081,234 examination procedure, dated Oct. 1, 1984, the Applicant (Tanabe) exhibited comparison data from which it is clear that reacting (II) and (III) in toluene, in the presence of KOH, the desired compound (IV) is formed in no small amounts, while operating with acetone, other conditions being equal, the same compound (IV) is obtained in a 86.2% yield.

According to the invention, (+)-cis-3-hydroxy-2,3-dihydro-2-(4-methoxyphenyl)-1,5-benzothiazepin-4(5H)one (II) is treated with a 1-1.5 molar amount of dimethylaminoethyl chloride, in the appropriate hydrochloride form, and with an excess of potassium carbonate (2-3 moles) in a toluene/water/solubilizing agent mixture (8:1:0.5-18:1:1 v/v), with catalytic amounts of one of the quaternary ammonium salts usually employed as catalysts in nucleophilic substitution reactions in phase-transfer conditions. Preferably, (II)/(III) molar ratio is about 1:1.2; (II)/$K_3CO_3$ molar ratio is about 1:2.3; the solvent mixture (toluene/$H_2O$/solubilizing agent) is used in amounts of about of 3.2-4 liters/mole of (II), being the toluene/$H_2O$/solubilizing agent volumetric ratio about 10:1:1, while tetrabutylammonium sulfate is the preferred quaternary ammonium salt, as above mentioned.

The react ion mixture is refluxed for 5-6 hours, whereupon the toluene phase containing (+)-cis-3-hydroxy-2,3-dihydro-2-(4-methoxyphenyl)-1,5-benzothiazepin-4(5H)-one (IV) is separated from the aqueous phase and directly subjected to acetylation.

The final product is obtained with very high yields and in an extremely pure form. Table I contains comparison data, referred to about 100 kg batches of intermediate (II) (i.e. industrial amounts), of the processes according to the prior art and according to the invention.

phase is sufficient. Compared to EP 0,158,303, the operation of substituting the reaction solvent with the acylation one is avoided, with evident time, labour and material costs saving.

d) The final product is already obtained in solution in the solvent suited to the final step (acetylation), in a different way from the prior art processes which carry out the first reaction step in a solvent different from the one of the final step.

e) The organic solvent in the process of the invention is easily recovered by washing with water and purifying by distillation.

f) The invention process, accordingly to the above-mentioned paragraph e), produces only aqueous wastes that can be sent to biological purification.

The processes according to U.S. Pat. No. 4,438,035 and EP 0,158,303 produce comparable amounts of waste sewage which are to be biologically purified and also a large amount of organic solvent which is to be incinerated as it cannot be recycled, due to the nature of the impurities therein contained, as outlined in the procedure. This is particularly serious in the EP 0,158,303 case because the organic solvent to eliminate is an halocarbon.

The enormous quantity of wastes to be incinerated from the process according to U.S. Pat. No. 3,562,257 (aside from the already above-mentioned drawbacks) makes unfeasible the process itself.

EXAMPLE 1

100 kg of (+)-cis-2-(4-methoxyphenyl)-3-hydroxy-2,3-dihydro-1,5-benzothiazepin-4(5H)-one are suspended in 900 l of toluene, 50 l of DMF and treated with 106 kg of $K_2CO_3$ and 63 kg of dimethylaminoethyl chloride hydrochloride and 50 g of tetrabutylammonium hydrogen sulfate. The suspension is heated to about 90° C. and 60 l of water are added. After 5 hours heating is interrupted. The reaction mixture is cooled to about 30° C., diluted with 500 l of water, partitioned and the organic phase is washed with water. The amount of compound (IV) present in the toluene phase is determined (kg 120, yield 97%); 180 kg of acetic anhydride

|  | Base | Solvent | yeild in comp. IV | Time (hours) | Water sewage | |
|---|---|---|---|---|---|---|
|  |  |  |  |  | to incinerator | to biological depuration |
| U.S. Pat. No. 3,562,257 | NaH | DMSO | 83.8% | 96 | 5600 | — |
| U.S. 4,438,035 | $K_2CO_3$ | Aceton/water | 91% | 60 | 900 | 1500 |
| EP-A2 0,158,303 | Ca(OH)$_2$ Ba(OH)$_2$ | methylene chloride | 93% | 51 | 2000 | 2100 |
| Example 1 of the present invention | $K_2CO_3$ | Toluene DMF/water | 97% | 36 | — | 1600 |

From data-table analysis, the invention process shows with clear evidence the following advantages:

a) The intermediate (IV) global yield is almost quantitative; this also means lower by-product formation, as to say a purer and easily to purified product.

b) Definitely shorter production times. Compared with the best of the two known methods a 30% saving is achieved, with an evident reduction in labour cost and equipment locking up.

c) Simpler operating method since, contrary to the U.S. Pat. No. 4,438,035 process, no solid by-products are obtained. A portion separation by centrifugation is therefore useless, and a simple decantation of an organic liquid phase from an aqueous are added and the reaction mixture is kept at room temperature for 10 hours.

The solution is concentrated recovering toluene and unreacted acetic anhydride; the residue is taken up into 400 l of acetone and Diltiazem hydrochloride is precipitated by cooling using gaseous HCl.

After filtration, the product is recrystallized from 600 l of butanol.

About 140 kg of Diltiazem are obtained.

EXAMPLE 2

50 g of (+)-cis-2-(4-methoxyphenyl)-3-hydroxy-2,3-dihydro-1,5-benzothiazepin-4(5H)-one are suspended in 450 ml of toluene, 25 ml of N,N-dimethylacetamide, and treated with 53 g of $K_2CO_3$ and 31 g of dimethylaminoethyl chloride hydrochloride and 250 mg of tetrabutylammonium hydrogen sulfate. The suspension is heated to about 90° C. and 30 ml of water are added. After 5 hours heating is interrupted. The reaction mixture is cooled to about 30° C., diluted with 25 ml of water, partitioned and the organic phase is washed with water. The amount of compound (IV) present in the toluene phase is determined (g 60.5, yield 98%); 90 g of acetic anhydride are added and the reaction mixture is kept at room temperature for 10 hours.

The solution is concentrated recovering toluene and unreacted acetic anhydride; the residue is taken up into 200 ml of acetone and Diltiazem hydrochloride is precipitated by cooling using gaseous HCl.

After filtration, the product is recrystallized from 300 ml of butanol.

About 70 g of Diltiazem are obtained.

EXAMPLE 3

50 g of (+)-cis-2-(4-methoxyphenyl)-3-hydroxy-2,3-dihydro-1,5-benzothiazepin-4(5H)-one are suspended in 450 ml of toluene, 25 ml of N-methyl-2-pyrrolidone, and treated with 53 g of $K_2CO_3$ and 31 g of dimethylaminoethyl chloride hydrochloride and 250 mg of tetrabutylammonium hydrogen sulfate. The suspension is heated to about 90° C. and 30 l of water are added. After 5 hours heating is interrupted. The reaction mixture cooled to about 30° C., diluted with 25 ml of water, partitioned and the organic phase is washed with water. The amount of compound (IV) present in the toluene phase is determined (g 61, yield 98,5%); 90 g of acetic anhydride are added and the reaction mixture is kept at room temperature for 10 hours.

The solution is concentrated recovering toluene and unreacted acetic anhydride; the residue is taken up into 200 ml of acetone and Diltiazem hydrochloride is precipitated by cooling using gaseous HCl.

After filtration, the product is recrystallized from 300 ml of butanol.

About 70.5 g of Diltiazem are obtained.

We claim:

1. A process for the preparation of (+)-cis-3-(acetoxy)-5-[2-(dimethylamino)-ethyl]-2,3-dihydro-2-(4-methoxyphenyl)-1,5-benzothiazepin-4(5H)-one hydrochloride of formula (I):

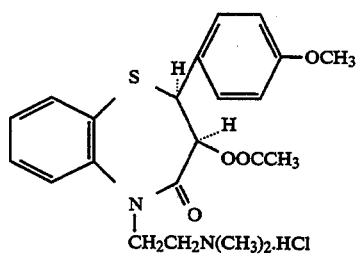

which consists of the steps of:

1) alkylating the benzothiazephine derivative of formula (II):

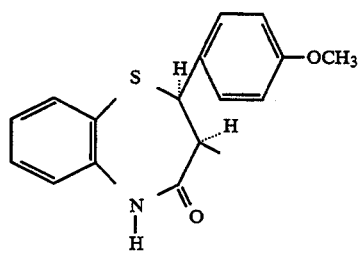

with dimethylaminoethyl chloride hydrochloride of formula (III):

under phase-transfer conditions, in toluene and water and in the presence of one solubilizing agent selected in the group consisting of dimethylformamide, N,N-dimethylacetamide and N-methyl-2-pyrrolidone, potassium carbonate as the base and a quaternary ammonium salt as the catalyst; whereby the intermediate of formula (IV) is obtained:

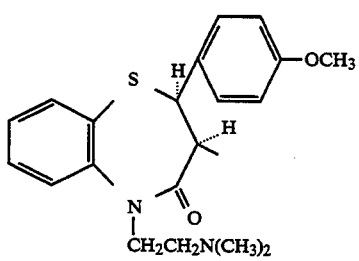

and said compound of formula (IV) is present in the toluene phase, 2) separating the toluene phase from the water phase;
3) and reacting said toluene phase containing said compound of formula (IV) with excess of acetic anhydride to obtain the compound of formula (V):

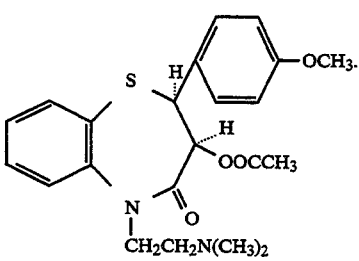

4) concentrating said toluene solution from step 3) to remove excess of acetic anhydride and toluene to obtain a residue;
5) dissolving said residue in acetone; and
6) passing gaseous HCl through said acetone solution from step 5) whereby said compound of formula I precipitates.

2. The process according to claim 1 wherein the toluene/$H_2O$/solubilizing agent volumetric ratio in step 1) is between 10:1:1 and 18:1:1.

* * * * *